United States Patent [19]
de de la Pena et al.

[11] Patent Number: 6,013,259
[45] Date of Patent: Jan. 11, 2000

[54] PATENT ON USE OF ALOE VERA OPHTHALMIC SOLUTION FOR TREATMENT OF THE DRY EYE SYNDROME, INFLAMMATIONS, ULCERATIONS, ALKALINE OR ACID BURNS, INFECTIONS, AND CATARACTS

[76] Inventors: Nuria E. A. C. de de la Pena, 1825 I St., NW Suite 400, Washington, D.C. 20008; Silvia Cristina Madoz, M.T. de Alvear, 1624 2do., Capital Federal 1060, Buenos Aires, Argentina

[21] Appl. No.: 08/939,470

[22] Filed: Sep. 22, 1997

[51] Int. Cl.$^7$ ..................................... A61K 35/78
[52] U.S. Cl. ........................ 424/195.1; 514/912
[58] Field of Search .......................... 424/195.1; 514/912

[56] References Cited

U.S. PATENT DOCUMENTS

| | | | |
|---|---|---|---|
| 3,878,197 | 4/1975 | Ray .......................................... | 201/160 |
| 3,892,853 | 7/1975 | Cobble ..................................... | 424/195 |
| 5,290,572 | 3/1994 | MacKeen ................................. | 424/687 |
| 5,487,899 | 1/1996 | Davis ..................................... | 424/195.1 |

OTHER PUBLICATIONS

Mortada et al., Use of Aloe Extracts in the Treatment of Experimental Corneal Ulcers, Cs. Oftal., 32, 1976, No. 6, p. 424–427.

Kotsche W., and Gottschalka, Enfermedades del conejo y de la liebre ,Edit Acribia, Zaragoza, España, 71, 1984.

Banks W.J., Histologia Veterinaria aplicada 658–681, 1986.

Smith S.E., Start dry eye therapy with an accurate diagnosis, Ocular Surgery News International vol. 9 N° . 9 (64–69) Sep. 1998.

Abrams, K.L., et al. , Evaluation of the Shirmer tear test in clinically normal rabbits, Am. J. Vet. Res., 51:12, 1912–1913, 1990.

Siganos C.S. et al. , Topical use of Zinc desferrioxamine for corneal alkali injury in a rabbit, Cornea 17Banks:191–195, 1998.

Chung J.H., Kang Y.G., Kim H.J. Effect of 0.1% dexamethasone on epithelial healing in experimental corneal alkali wounds during the repair process, Graefes Arch. Clin. Exp. Ophthalmol., 236(7), 537–545, 1998.

de la Peña N. and Madoz S.C., Tratamiento del Sindrome de Ojo Seco con un Colirio de Alo Vera, Curso Annual de Perfeccionamiento para graduados de la Sociedad Argentina de Oftalmologia, Jul. 23–24, 1998, 1* Premio SAO 1998, Concurso de Posters.

Shein O.D. et al. , Prevalence of dry eye among elderly, Am. J. of Ophthalmol., 124:723–728, 1997.

Shein O. D. et al. , Relation between signs and symtons of dry eye in the elderly, Ophthalmology, 104\9, 1395–1400, 1997.

Embase Abstract 78049610 (1976). Mortada et al.

*Primary Examiner*—Zohreh Fay

[57] ABSTRACT

This invention relates to a process for obtaining Aloe Vera gel and the ophthalmic use of Aloe Vera gel in the treatment of dry eye syndrome.

4 Claims, No Drawings

PATENT ON USE OF ALOE VERA OPHTHALMIC SOLUTION FOR TREATMENT OF THE DRY EYE SYNDROME, INFLAMMATIONS, ULCERATIONS, ALKALINE OR ACID BURNS, INFECTIONS, AND CATARACTS

BACKGROUND OF THE INVENTION

The dry eye syndrome is a very common disorder that affects mainly contact lens users, and post-menopaual women. It is also known as keratoconjuntivitis sicca. This disorder induces a feeling of dryness, burning, redness, and a persistent irritation of the eye. In severe cases it can produce pain, photophobia, corneal ulceration, severe inflammation, loss of vision, and develop of opportunistic infections.

BRIEF SUMMARY OF THE INVENTION

The investigation into the use of aloe Vera in ophthalmologic disorders was aimed at examining whether the rapid tissue repairing and anti-inflammatory properties of aloe Vera, which have been successfully demonstrated in the treatment of internal and external wounds, could be applied to disorders of the eye involving inflammation, ulceration and infections.

Current available treatments for the dry eye are not fully effective because they do not induce re-epithelization of the cornea and repairing of the physiology of the eye. In this cases is common the use of corticosteroids to decrease inflammation, thus impairing local immunity. This situation facilitates the onset of opportunistic and chronic infections. The persistent irritation caused because the fail in lubrication between the eyes' lid and the eye surface may also trigger Herpes virus (HSV) recurrence.

The Aloe Vera gel has proved effective in the treatment on internal and external wounds because of its following properties: analgesic, anti-inflammatory, aids in cell penetration of source compounds, stimulates fibroblasts to produce collagen and proteoglycanes as to build new tissue in the affected area, regenerates epithelium, increases immunity, causes no collateral effects and is non toxic.

The above mentioned properties of the Aloe Vera gel are very valuable in ophthalmology because of the lack of an effective treatment for the following different pathologies: dry eye, viral keratoconjuntivities, corneal ulcers, keratitis, alkaline or acid burns, recurrent corneal ulcers. We propose the use of Aloe Vera gel eye drops in all this pathologies, because of the repairing properties of the Aloe Vera, the rapid response of the patient (decrease pain and inflammation), because it has no collateral effects, it is easy to administer, it is inexpensive, and the treatment involves less frequent applications than other therapies.

For the treatment of the dry eye syndrome there are very many artificial tears all with different characteristics trying to imitate natural tears quality and activity. The main difficulty they show is its quick elimination of the ocular globe, thus a very frequent application of the eye drops is needed, and even so there are not a solution on serious pathologies. In these cases we used eye drops with a solution of Aloe Vera gel in a patient with Sorgen's syndrome. Immediately in the first 48 Hs. the referred decreased pain, erithema and inflammation.

Patients carrying a viral keratitis infection showed that the Aloe Vera treatment could alleviate the symptoms very quickly, and a regression of the process was obtained in a shorter time.

In cases with very important corneal ulcers that usually take long scarification times, we observed that the Aloe Vera drops treatment induced a better and more rapid scarification. The indication for the application of the eye drops was no more than four times a day during wake hours.

No patient referred annoyance during the application of the eye drops and no side effects were observed in any patient.

We tried also the eye gel preparations on patients with important corneal ulcers. The gel was applied twice a day and the eye was occluded for 72 Hs. After removing of the bandages we continued the treatment with the eye drops preparation. We observed diminished pain and inflammation, and a shorter time to totally cure the ulcers.

The ointment Aloe Vera preparation for the eyes was assayed in several patients who suffered mild and severe alkaline or acid burns derived from work accidents. The ointment was applied one or two times a day (depending of the severity of each case). In all cases the eye was occluded several days (72 Hs. to 7 days). After the bandages were removed the treatment was followed with the Aloe Vera eye drops preparation until the total healing of the lesions.

Pain relief was the first parameter referred by the patient. Redness irritation and inflammation decreased after the first 48 Hs. Shorter times to total reepithelization of the corneal ulcers were observed. Total recovery of the vision was obtained from 10 to 15 days for the mild cases, and in 30 to 45 days in severe cases.

An antibiotic adjuvant therapy was applied in same cases that showed an aggregated bacterial infection. The cream preparation was used after removing of the bandages to externally treat the eyes' lids. We obtained a quick relief of the skin inflammatory symptoms (redness, slowness, exfoliation) and a very good reepithelization of the eye lids skin.

We conclude that the use of the Aloe Vera in different ophthalmologic pathologies would be a great goal for the medicine because it will fill up an important gap of the ophthalmic therapy.

DETAILED DESCRIPTION OF THE INVENTION

Preparation of the Aloe Vera gel eye drops:

The extraction of the Aloe Vera gel from the plants was done through the hand filleting method The Aloe Vera leaves were processed as soon as possible after cutting from the plant. The whole extraction process takes no more than 2 hrs. The leaf removed from the plant was washed with a chlorinated solution rinsed with sterilized water and dried. Then the gel is separated from the leaf peeling away the outer green cortex of the leaf. Carefully but consistently close, not to lose the region just below the skin that contains substantial quantities of a highly active mucopolysaccharide composition. The separated gel matrix is immediately stabilized with 0.1% of citric acid and 0.2% potassium sorbate.

Homogenization was performed using a high-speed blender. The preparation was then fractionated and readily freeze at −18 centigrade. For the preparation of the final Aloe Vera gel solution the frozen homogenate was towed, clarified, centrifuged at 10000 rpm in a continues flow centrifuge and filtered through a $0.2\mu$ pore filtration system.

The final 40:1 Aloe Vera solution was sterile, aloin free, pulp free and mucilage free.

The specific activity controls were done according to the International Aloe Science Council (IASC) recommendations.

The eye drops were prepared using the final Aloe Vera solution in concentrations ranging from 6% to 30% in deionizated sterile water 0.2% potassium sorbate was added as a conservative, and the pH was adjusted to 7.1.

The gel for the ocular use with an Aloe Vera solution was prepared with Natrosol HHR-P250 (hydroxiethycellulose purified from Hercules Acuolom) 0.75% in deionized water with 0.2% of potassium sorbate as a preservative.

The Aloe Vera 40:1 solution was added at any required concentration ranging from 6 to 30% reaching the gel room temperature. The pH was adjusted to 7,1.

The ointment utilized was the one described in U.S. Patent No. 4,725,438 of Billie S. Leazer 1988. It is Aquaphor a mixture of equal parts of petrolatum, mineral oil, mineral wax, and wool wax alcohol, that provides a suitable base for the Aloe Vera ointment.

The concentration of the Aloe Vera 40:1 in the ointment base was 8% .The pH of the ointment was adjusted to 7.1

The cream used was hydro-soluble base. Propyl and methylparabene were used as conservatives. The Aloe Vera 40:1 concentration added was the 6%. The pH was adjusted to 5.5 to meet the external skin pH requirements.

We claim:

1. A method for treating a patient afflicted with dry eye comprising the steps of:

a) Providing Aloe Vera based ophthalmic compositions comprising ophthalmologically acceptable Aloe Vera gel, diluted in ophthalmologically acceptable carriers, b) Applying said Aloe Vera ophthalmic composition adjacent to lateral or inferior lid margins exterior to an ocular surface in a sufficient amount and for sufficient time to alleviate dry eye, wherein blinking action of the lid margins cuts off and carries into the eye small amounts of the composition thereby effecting treatment of the dry eye condition.

2. The method of treating a patient afflicted with dry eye of claim 1 wherein said ophthalmologically acceptable carrier is hydrophilic.

3. The method of treating a patient afflicted with dry eye of claim 1 wherein said ophthalmologically acceptable carrier is distilled water, hydroxiethylcellulose purified, or petrolatum.

4. The processing of an ophthalmologically acceptable stabilized and sterile Aloe Vera gel by freezing and thawing the gel within 2 hours from the time of having cut the leaves from the plant, and by adding citric acid and potassium sorbate to stabilize the gel.

* * * * *